(12) United States Patent
Kuzma

(10) Patent No.: US 7,047,081 B2
(45) Date of Patent: May 16, 2006

(54) BAND TYPE MULTICONTACT ELECTRODE AND METHOD OF MAKING THE SAME

(75) Inventor: Janusz A Kuzma, Parker, CO (US)

(73) Assignee: Advanced Bionics Corporation, Valencia, CA (US)

( * ) Notice: Subject to any disclaimer, the term of this patent is extended or adjusted under 35 U.S.C. 154(b) by 494 days.

(21) Appl. No.: 10/600,381

(22) Filed: Jun. 20, 2003

(65) Prior Publication Data

US 2004/0015221 A1 Jan. 22, 2004

Related U.S. Application Data

(62) Division of application No. 09/970,406, filed on Oct. 2, 2001, now abandoned.

(60) Provisional application No. 60/239,154, filed on Oct. 10, 2000.

(51) Int. Cl.
*A61N 1/04* (2006.01)

(52) U.S. Cl. ..................................... 607/115

(58) Field of Classification Search ................ 607/1, 607/115–117, 122, 137
See application file for complete search history.

(56) References Cited

U.S. PATENT DOCUMENTS

| 3,724,487 A | 4/1973 | Avery et al. |
| 4,437,474 A | 3/1984 | Peers-Trevarton |

(Continued)

OTHER PUBLICATIONS

Kuzma, Harrison, and Smith inventors for U.S. Appl. No. 10/000,408; filed Nov. 2, 2001; entitled "Multicontact Electrode Array and Method of Making the Same".

(Continued)

*Primary Examiner*—Scott M. Getzow
(74) *Attorney, Agent, or Firm*—Bryant R. Gold; Victoria A. Poissant

(57) ABSTRACT

A multicontact electrode array suitable for implantation in living tissue includes a distal end having multiple spaced-apart ring or band electrode contacts carried on a flexible tube carrier. Each ring electrode contact is laser welded to a respective wire tip that has a multi-helix orientation on the inside of a separation tube. The center of the multi-helix wire defines a lumen wherein a positioning stylet, or other suitable positioning tool, may be removably inserted when the electrode array is implanted. The method of making the multicontact electrode array includes, as an initial step, winding lead wires around a suitable mandrel so as to form a multi-helix configuration. (Alternatively, the wire may be purchased in a multiwire pre-wound configuration that defines a lumen, in which case the mandrel is slipped inside the lumen.) Then, at a distal end of the electrode, each wire within the multi-helix winding is unwound so as to protrude out from the winding. Next, a non-conductive separation silicone tube which has a longitudinal slit along its length, is placed around the wound wires. Ring contacts are then placed over the silicone tube at a distal end of the electrode array and spaced apart as desired. These ring contacts also have a slit therein through which the protruding wire ends may exit. The silicone tube is used as a spacer to centrally locate the multi-helix wound wires with the ring contacts. A compressive die may be used to hold the pre-assembled ring contact, multi-helix wire, separation tube in their desired positions, and may be used to close the opening or slit of each ring contact through which the wire tips protrude. The wire tips are then individually trimmed to a suitable distance. A laser welding process may then be used to bond each lead wire to a corresponding ring contact. Finally, the preassembled electrode array is placed in a molding die, and a polymer filler is injected into the internal gaps of the electrode array components.

10 Claims, 9 Drawing Sheets

U.S. PATENT DOCUMENTS

| | | |
|---|---|---|
| 4,444,195 A | 4/1984 | Gold |
| 4,559,951 A | 12/1985 | Dahl et al. |
| 4,819,647 A | 4/1989 | Byers et al. |
| 4,840,186 A | 6/1989 | Lekholm et al. |
| 4,944,088 A | 7/1990 | Doan et al. |
| 5,097,843 A | 3/1992 | Soukup et al. |
| 5,201,903 A | 4/1993 | Corbett, III et al. |
| 5,267,564 A | 12/1993 | Barcel et al. |
| 5,423,763 A | 6/1995 | Helland et al. |
| 5,447,533 A | 9/1995 | Vachon et al. |
| 5,458,629 A | 10/1995 | Baudino et al. |
| 5,466,253 A | 11/1995 | Doan |
| 5,658,263 A | 8/1997 | Dang et al. |
| 5,658,709 A | 8/1997 | Layman et al. |
| 5,728,063 A | 3/1998 | Preissman et al. |
| 5,755,766 A | 5/1998 | Chastain et al. |
| 5,833,714 A | 11/1998 | Loeb |
| 6,052,625 A | 4/2000 | Marshall |
| 6,066,166 A | 5/2000 | Bischoff et al. |
| 6,070,105 A | 5/2000 | Kuzma |
| 6,112,124 A | 8/2000 | Loeb |
| 6,167,314 A | 12/2000 | Fischer, Sr. et al. |
| 6,216,045 B1 | 4/2001 | Black et al. |
| 6,522,932 B1 | 2/2003 | Kuzma et al. |

OTHER PUBLICATIONS

Faltys, Griffith, and Harrison inventors for U.S. Appl. No. 09/823,271; filed Mar. 30, 2001; entitled "High Contact Count, Sub-Miniature, Fully Implantable Cochlear Prosthesis".

BAND TYPE MULTICONTACT ELECTRODE AND METHOD OF MAKING THE SAME

The present application is a Divisional of U.S. application Ser. No. 09/970,406, filed Oct. 02, 2001 now abandoned; which claims the benefit of U.S. Provisional Application Ser. No. 60/239,154, filed Oct. 10, 2000, which applications are incorporated herein by reference.

BACKGROUND OF THE INVENTION

The present invention relates to the field of implantable electrodes, and more particularly to a multicontact band type electrode array. In a preferred embodiment, such multicontact band type electrode array is used with an implantable stimulator to provide electrical stimulation to body tissue, for example, to brain tissue for brain stimulation, to selected nerves for neural stimulation, or to the spinal cord for spinal cord stimulation (usually done to control or manage pain). Additionally, the present invention further provides a simple and reliable method of constructing a multicontact band type electrode array.

Spinal cord and other stimulation systems are known in the art. For example, U.S. Pat. No. 3,724,467, teaches an electrode implant for the neuro-stimulation of the spinal cord. A relatively thin flexible strip of physiologically inert plastic is provided as a carrier on which a plurality of electrodes is formed. The electrodes are connected by leads to an RF receiver, which is also implanted, and which is controlled by an external controller.

In U.S. Pat. No. 5,458,629, a method of making an implantable ring electrode is taught. The method disclosed in the '629 patent describes an electrode array with a first lumen containing electrical conductors and a second lumen adapted to receive a stylet. In contrast, the multicontact electrode array of the present invention requires only one lumen, and thus the fabricating steps described in the '629 patent differ from those taught by the present invention. Moreover, the '629 patent teaches that notches must be formed in the lead body to position the electrode members, whereas the present invention does not require such notches.

Other implantable electrodes, electrode arrays, and features of implantable electrodes are taught, e.g., in U.S. Pat. No. 5,097,843 (a porous electrode); U.S. Pat. No. 5,267,564 (a built-in sensor); U.S. Pat. No. 5,423,763 (a suture sleeve for anchoring the lead body); U.S. Pat. No. 5,447,533 (a combination electrode and drug delivery system); U.S. Pat. No. 5,466,253 (a crush resistant multiconductor lead body); U.S. Pat. No. 4,819,647 (a spirally-shaped electrode array); U.S. Pat. No. 5,833,714 (electrodes made from tantalum); U.S. Pat. No. 6,112,124 (electrodes separated by dielectric partitions or fins); and U.S. Pat. No. 6,070,105 (modiolus-hugging electrodes for insertion into cochlea). The materials from which an implantable electrode array is made, including many of the manufacturing techniques, disclosed in these patents may also be used with the present invention. For that reason, the patents listed in this paragraph are incorporated herein by reference.

However, despite the various types of implantable electrode arrays known in the art, significant improvements are still possible and desirable, particularly relating to reducing costs and providing a more reliable construction based on new manufacturing technology.

Most designs of electrodes and connectors, for example, are based on the principle of molding a contact or array of contacts, usually made from biocompatible metal, into a polymer carrier, such as silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required. One of the main problems encountered in the fabrication of such electrodes or connectors is to find a reliable method of holding the system of contacts in the desired and stable position during the process of welding the connecting wires and during the process of molding the polymer carrier. A further problem relates to maintaining a controlled surface of the contacts that are to remain exposed, i.e., to ensure that the contacts are not covered by the polymer when the carrier is molded.

It is thus seen that there is a continual need for improved, more reliable, implantable multicontact electrode arrays that are simpler to make and less costly to make.

SUMMARY OF THE INVENTION

The present invention addresses the above and other needs by providing a simple and reliable method of constructing a multicontact electrode array.

The present invention focuses on the construction of the distal end of the electrode array where the electrode contacts are positioned in a specified spaced-apart relationship.

The invention disclosed and claimed herein provides a simple and reliable method of construction for a multicontact band type electrode. Advantageously, during the construction of such electrode, a central lumen is formed in the electrode array lead body. This lumen serves the purpose of providing access for a stylet to be used in conjunction with the lead during implantation of the electrode to the stimulating area. The electrode array may be constructed to have various ring contacts, depending on the application for which the electrode array is to be used, e.g., brain stimulation, neural stimulation, or spinal cord stimulation. Most of the electrode arrays used for such applications employ between 4 and 16 electrodes, and the arrangement of the electrodes can vary. For example one known arrangement is the paddle type electrode array. Electrodes of the paddle type array, are arranged in two or more parallel columns, permitting stimulation to be driven across an adjacent electrode. Another type of known arrangement positions the electrodes in a row, or "in line," along the longitudinal axis of a small diameter lead body. This in-line electrode arrangement allows the array to be inserted into the stimulating area, in a minimally invasive procedure, through the use of a large diameter needle and through the guidance of a stylet inserted in the lumen of the electrode array.

The present invention relates to the electrodes that are organized in a row, or "in line," and more particularly to a method of construction for making such electrodes. The simplified construction method provided by the invention advantageously reduces material costs, simplifies manufacturing processes, and thus reduces manufacturing time and labor costs.

The method of making an electrode in accordance with the invention includes, as an initial step, winding lead wires around a suitable mandrel so as to form a multi-helix configuration. (Alternatively, the wire may be purchased in a multiwire pre-wound configuration that defines a lumen, in which case the mandrel is slipped inside the lumen.) Then, at a distal end of the electrode, each wire within the multi-helix winding is unwound so as to protrude out from the winding. Sufficient unwinding is performed for each wire so that the protruding ends are spaced apart longitudinally a desired amount. Next, a non-conductive separation silicone tube is placed around the wound wires. Such silicone tube will typically have a longitudinal slit along its length through which the protruding wire ends may exit. Ring contacts are then placed over the silicone tube at a distal end of the electrode array and spaced apart as desired. These ring contacts also have a slit therein through which the protruding wire ends may exit. The silicone tube is used as a spacer to centrally locate the multi-helix wound wires with the ring contacts. If a thicker insulated wire is used, then the separation tube may not be required. A compressive die may be used to hold the pre-assembled ring contact, multi-helix wire, and separation tube in their desired positions. Such compressive die also may be used to close the opening or slit of each ring contact through which the wire tips protrude. The wire tips are then individually trimmed to a suitable distance. A laser welding process may then be used to bond each lead wire to a corresponding ring contact. The mandrel is then replaced by a molding stylet, where such stylet is used to help keep the central lumen free from the polymer filler material. The preassembled electrode array is placed in a molding die, and a polymer filler is injected into the internal gaps of the electrode array components. The polymer filler is allowed to cure and the molding stylet is removed from the distal end of the assembled electrode array. Finally, the distal opening is sealed with a liquid polymer or precured sealing plug which may be made from the same filler material.

The construction method of the present invention is more simplified than others known in the art, and hence provides a more reliable construction method with higher yield rates. All this, in turn, lowers the overall cost to manufacture the multicontact electrode array.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches a manufacturing technique for an implantable electrode array having multiple ring (or band) contacts. Typically, each ring or band contact is evenly spaced along the longitudinal axis of the lead, although unevenly spaced contacts could also be made.

Figure 1:
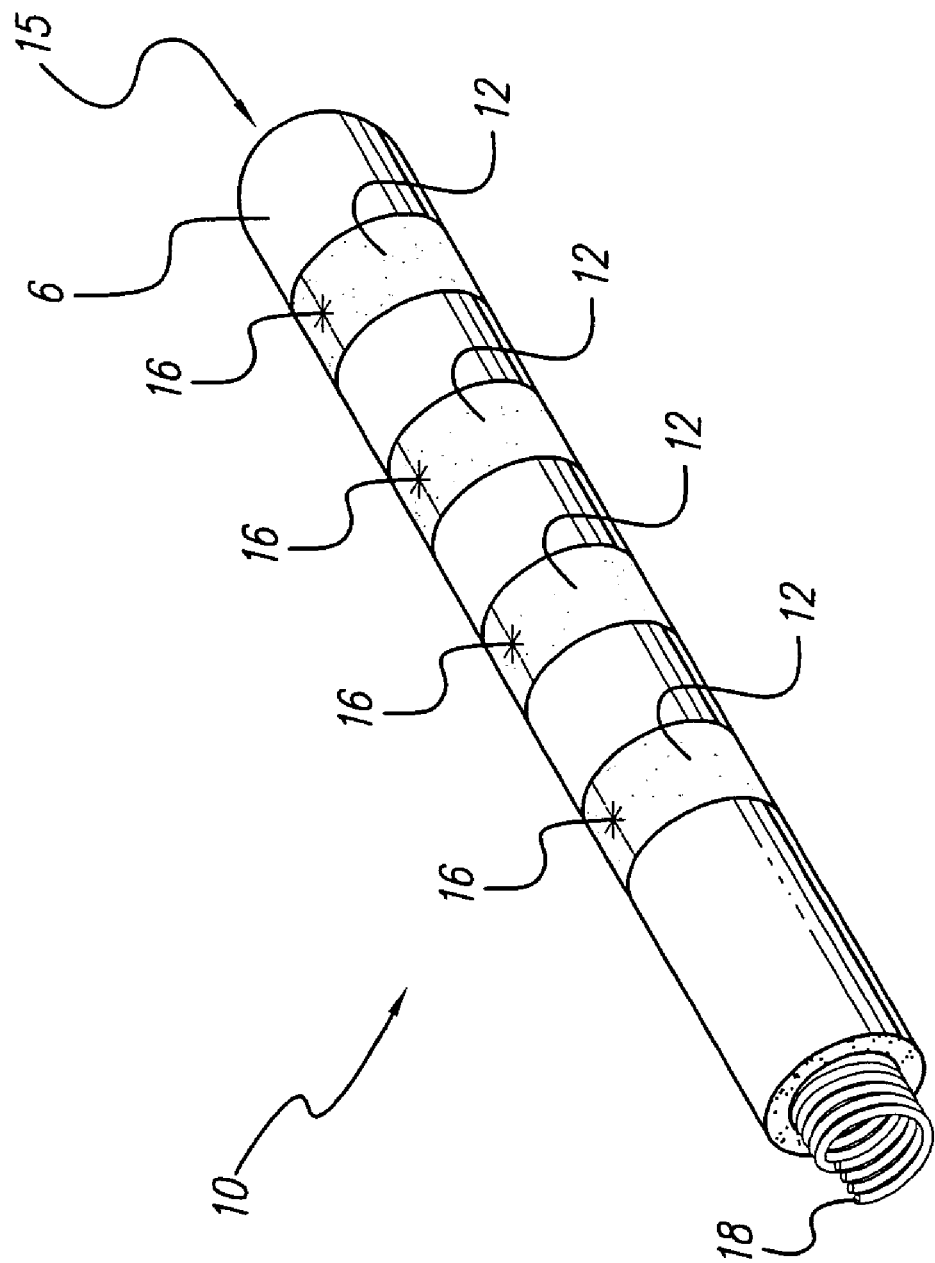
FIG. 1 is a perspective view showing a preferred embodiment of the multicontact band type electrode array.

FIG. 1 shows a preferred embodiment of an electrode array 10 with four ring contacts 12 made in accordance with the invention. The number of contacts can vary depending on the purpose for which the electrode array is to be used. The electrode array of the present invention may be used with any suitable implantable pulse generator, and may have as few as one contact, or as many as 30 contacts. Typically, for most applications, the number of contacts will vary from one to eight.

As seen in FIG. 1, a partial perspective view of the electrode array 10 is shown with four ring contacts 12 and four corresponding laser spot welds 16 where four respective wires are electrically connected to the ring contacts. The technique or method used in making the electrode array 10 comprises the following described manufacturing steps. Advantageously, it is a simple and reliable technique that can be carried out using simple materials, processes, and equipment, and when used provides a high manufacturing yield rate. Because the method is relatively easy to use, it allows a band type multicontact electrode to be made relatively inexpensively.

The simple process and preferred method of making the electrode array 10 is best understood in connection with the description of significant features of the multicontact electrode shown in FIGS. 2 through 8.

Most designs of electrodes and connectors are based on the principle of molding a contact or array of contacts, usually made from biocompatible metal, into a polymer carrier, such as silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required. One of the main problems encountered in the fabrication of such electrodes or connectors is to find a reliable method of holding the system of contacts in the desired and stable position during the process of welding. Moreover, the welding process itself is also a problem because the welds are not made consistent nor reliable in all of the contacts formed. A further problem is found during the process of molding the polymer carrier and maintaining a controlled surface of the contacts that are to remain exposed, i.e., to ensure that the contacts are not covered by the polymer when the carrier is molded.

The preferred method of making the electrode array 10 described below in connection with FIGS. 2 through 8 is based on the principle of attaching (by the process of laser spot welding) electrode ring contacts made from precious, biocompatible material (such as platinum or one of its alloys) to the lead wire, also typically made from platinum, titanium, stainless steel, or alloys thereof. Laser spot welding advantageously provides a secure electrical attachment of the electrode material to the wire (consistently fusing the wire material to the ring contacts), and assures a secure mechanical attachment of the electrode material to the tube carrier.

Figure 3:
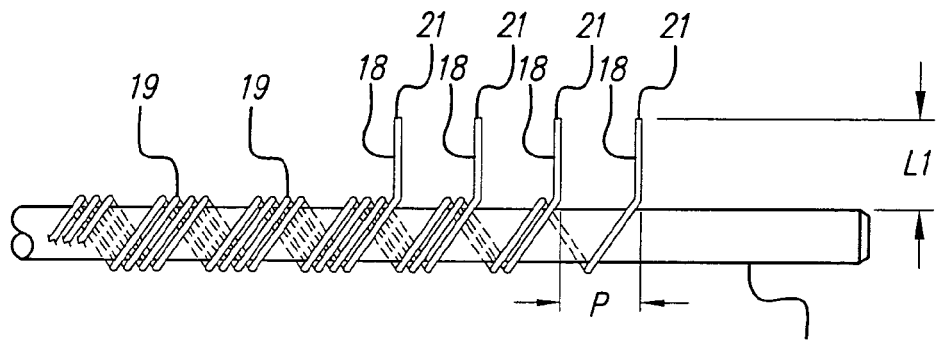
FIG. 3 depicts the preparation of the multiwire lead by placing prefabricated multiple helical wires around a suitable mandrel and unwrapping the distal ends of the wires by pointing them radially away from the mandrel.

To illustrate the manufacturing method, such method will be described relative to the fabrication of the electrode array 10. As a first step, as shown in FIG. 3, a multiple number of insulated lead wires 18 are wound around a mandrel 20 in a multi-helix orientation 19. (Alternatively, a multiple number of insulated pre-wound wires may be obtained in a multi-helix orientation.) A distal end of each wire is unwrapped and shaped as shown in FIG. 3 with a required pitch P between the tips of the unwrapped wire and leaving an excess distance L1 at the initial contact point. (This initial contact point, as will be evident from the description that follows, represents the distal end of the wire and electrode array. The excess wire that extends out from the mandrel the distance L1 may also be referred to as a "pigtail".) The distance L1 must initially be about 1.0 mm to allow assembly of the ring contacts and manipulation of the desired position of the ring contacts 12 with respect to the wires 18. The starting point of the second wire will be after the first helix turn, pitch P, of the first wire, as shown in FIG. 3. Each successive wire will then follow the same pattern until enough lead wires 18 are represented for the required number of ring contacts in the electrode array. As an example, FIG. 3 shows a section of four lead wires 18 wound in a helix pattern 19. The mandrel 20 is used for supporting the orientation of the wires as they are wound, to facilitate unwrapping the distal ends of the wires, to support assembly of the contact rings, and for forming the lumen 34 in the longitudinal axis of the helical wound wires. Such mandrel 20 typically has a diameter between about 0.3 mm to 0.5 mm. The formed central lumen 34, with a similar diameter of 0.3 mm to 0.5 mm, may be used for the purpose of directing or positioning the electrode array 10 into the stimulating area using an insertion stylet or other type instrument as known in the art of positioning electrode arrays.

Figure 3A:
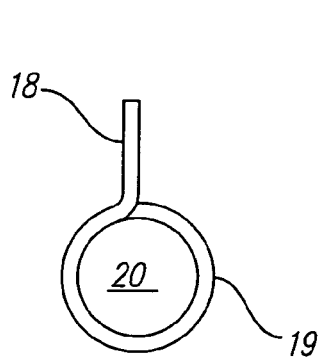
FIG. 3A depicts the side view of FIG. 3, showing the distal ends of the wires aligned in a vertical arrangement.
Figure 3B:
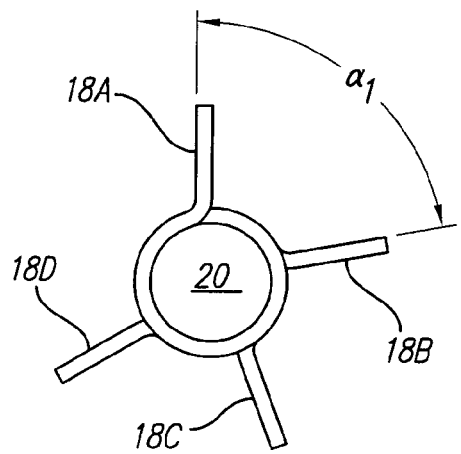
FIG. 3B depicts another side view of FIG. 3, where the distal ends of the wires are shown to be arranged at different non-aligned angles.

FIG. 3A shows a side view of FIG. 3 in which the ends of the lead wires 18 are vertically aligned. This is the optimal arrangement and makes the crimping process of the ring contacts, described below, a much easier task. However, to obtain the required pitch P, it is anticipated that the ends of the lead wires may not end up unwrapped in a vertical orientation, but rather in a non-aligned arrangement as shown in FIG. 3B. The most important objective is to unwrap the ends of the lead wires 18 so that they have substantially the same pitch P between each unwrapped wire tip 21. The process which comes later in the crimping process of the ring contacts can easily be done by rotating the pre-assembled electrode array to the required angle $\alpha 1$, when using the compressive die. This step will be explained in more detail below.

The initial end 21 (or pigtail end) of each lead wire is trimmed at a further step of the manufacturing process, as explained below.

Figure 4B:
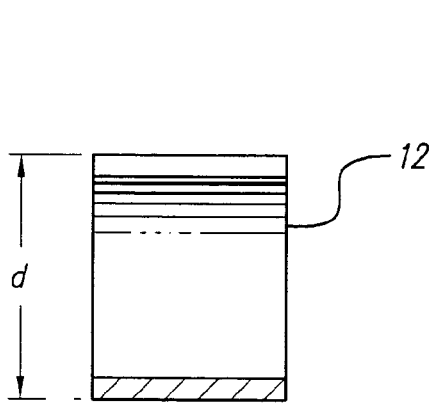
FIG. 4B is a sectional view of the open ring contact shown in FIG. 4A.
Figure 4A:
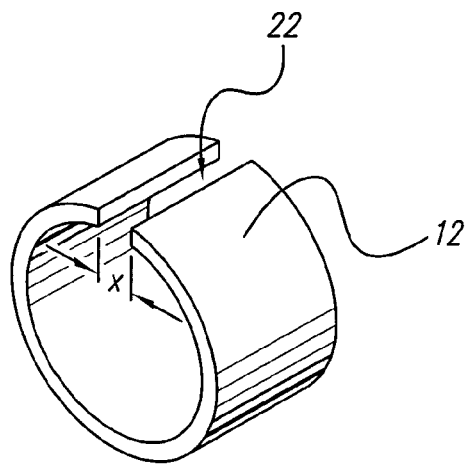
FIG. 4A shows a perspective view of an open ring contact used with the array.

The second main step of the manufacturing process of the electrode array 10 requires sizing the open ring contact 12 shown in FIG. 4A and FIG. 4B. The ring contacts 12 are made from any suitable biocompatible implantable conductive material (such as platinum or its alloys). The ring contact 12 may be made from a softer material then the material of the multi-helix wires 18. The size of the open gap 22 is made according to the following equation, x=2÷3d, where x is the gap distance shown in FIG. 4A and d is the diameter of the contact ring. Typically when x=0 (gap x is closed) the known value of d is 1.20 mm, which is the final diameter of the electrode array. The thickness of the ring material, for the embodiment shown in FIGS. 4A and 4B, is about 0.1 mm and the length of the ring contact is about 1.0 mm. After assembly, the ring contacts have a pitch P=2.0 mm. (These dimensions, of course, may be changed as needed depending upon the application for which the lead will be used.) Preferably, all required ring contacts are the same.

Figure 5A:
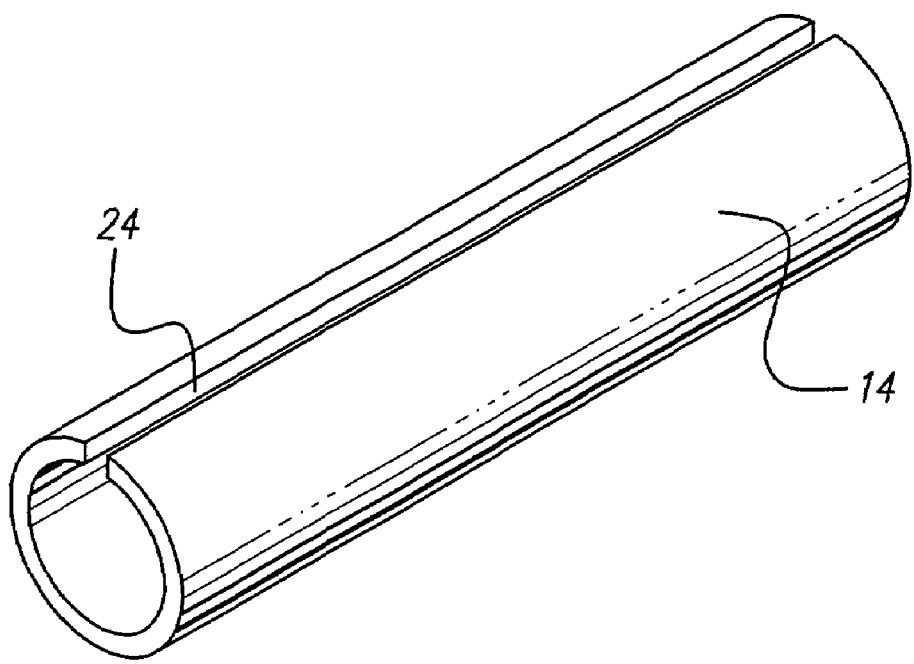
FIG. 5A is a perspective view of a separation tube that is used during the formation of the lead, showing an open longitudinal slit.
Figure 5B:
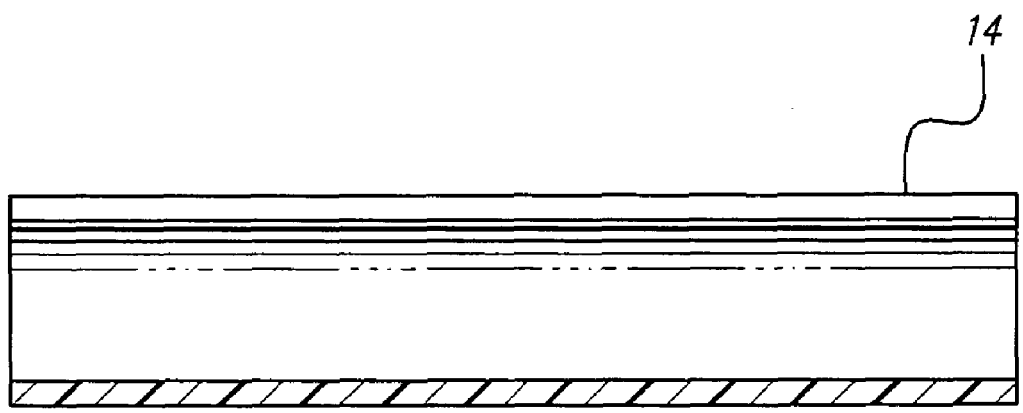
FIG. 5B is a sectional view of the separation tube of FIG. 5A.

The third main step of the manufacturing process of the electrode array 10 requires sizing a separation tube 14 shown in FIG. 5A and FIG. 5B. The separation tube 14 serves the purpose of separating the helical wound lead wires 18 from the ring contact 12, and keeps the helical lead wires in the center of the array. The separation tube may be made from any suitable non-conductive material, such as silicone. It extends along the full length of the electrode array. Alternatively, the separation tube 14 extends the length of the electrode array positioned at the distal end of the lead. Typical dimensions for the separation tube 14, for the embodiment shown in the figures, are as follows: length=10.0 mm, outside diameter=1.0 mm, and inside diameter=0.6 mm. Short individual sections of the silicone separation tube 14 for each individual ring contact 12 can also be used when the protruding lead wires are arranged in a non-aligned orientation as shown in FIG. 3B. A slit 24 is made to the entire length of the separation tube 14, or at least the entire length of the electrode array portion of an array/lead assembly, or to the short individual sections, if used. When the lead wires are assembled into the separation tube 14, the slit 24 allows access to the ends (or pigtails) of the lead wires. The slit 24 also allows access for the filler material to go through the internal gaps in the electrode array components. Adding the filler material will be explained at a further step below. If an insulated wire having a thick insulation is used, and there is no gap between the multi-helix wires and the ring contacts, then the separation tube may be omitted in the lead portion of an array/lead assembly.

A proximal end of the electrode array may include a connector to allow the wires 18 to be detachably electrically connected to a suitable pulse generator (not shown in the drawings). Alternatively, the proximal end of the wires 18 may be connected to a feedthrough pin, or other electrical contact point included in or on the pulse generator, in conventional manner, without the use of a detachable connector.

Figure 6A:
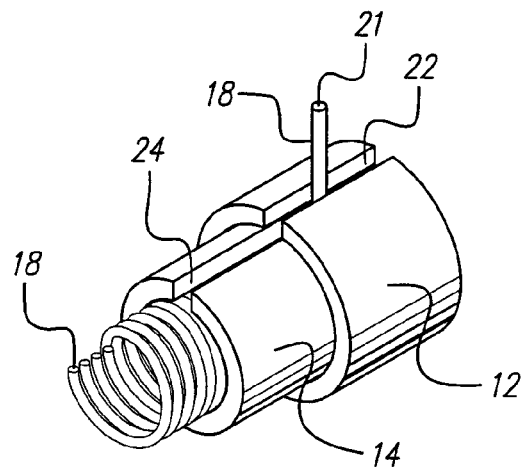
FIG. 6A is a partial perspective view of the assembled wires, open ring contacts, and separation tube.

Once the lead wires ends are formed to the required pitch P and the ring contacts 12 and separation tube 14 sized, the assembly process of these parts can take place. FIG. 6A shows a partial perspective view of these parts assembled together. Also shown in FIG. 6A is the gap 24 from the separation tube 14 which will be filled with a polymer as a final step for sealing the assembled electrode array 10. The filling process of the polymer will be explained below in connection with FIG. 8B. The distal (or pigtail) end 21 of one of the lead wires 18 is also shown in FIG. 6A, protruding radially from the gap 24 of the separation tube 14 and the gap 22 of the ring contact 12.

Figure 6B:
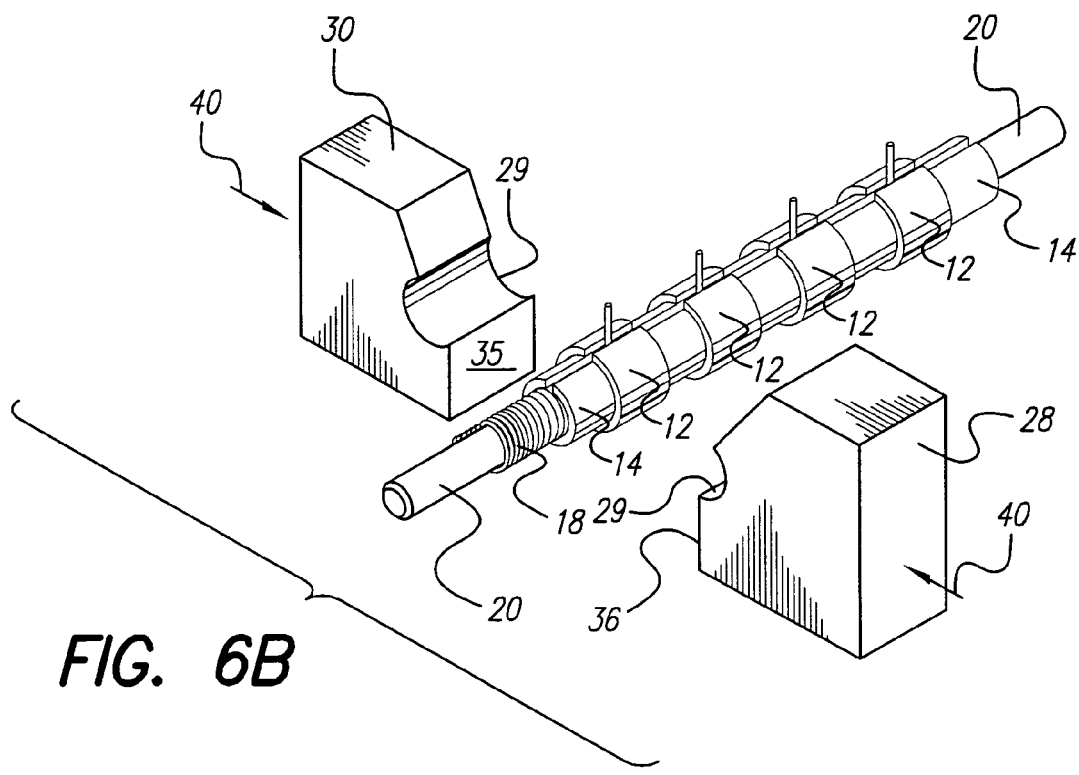
FIG. 6B shows an exploded view of the assembly of FIG. 6A and a compressive die.

Turning next to FIG. 6B, there is shown an exploded view of a compressive die and the electrode assembly. The compressive die consists of two plates; left side plate 28 and right side plate 30. Both the left and right plates have a half circular opening 29. When these openings come in contact, they make a channel 31 for positioning the preassembled electrode array. The arrows 40 indicate the direction of a compressive force applied to the die. When such force is applied, the left and right plates come in contact with each other at planes 35 and 36 and the electrode array is positioned within the channel 31 between both plates.

Figure 7A:
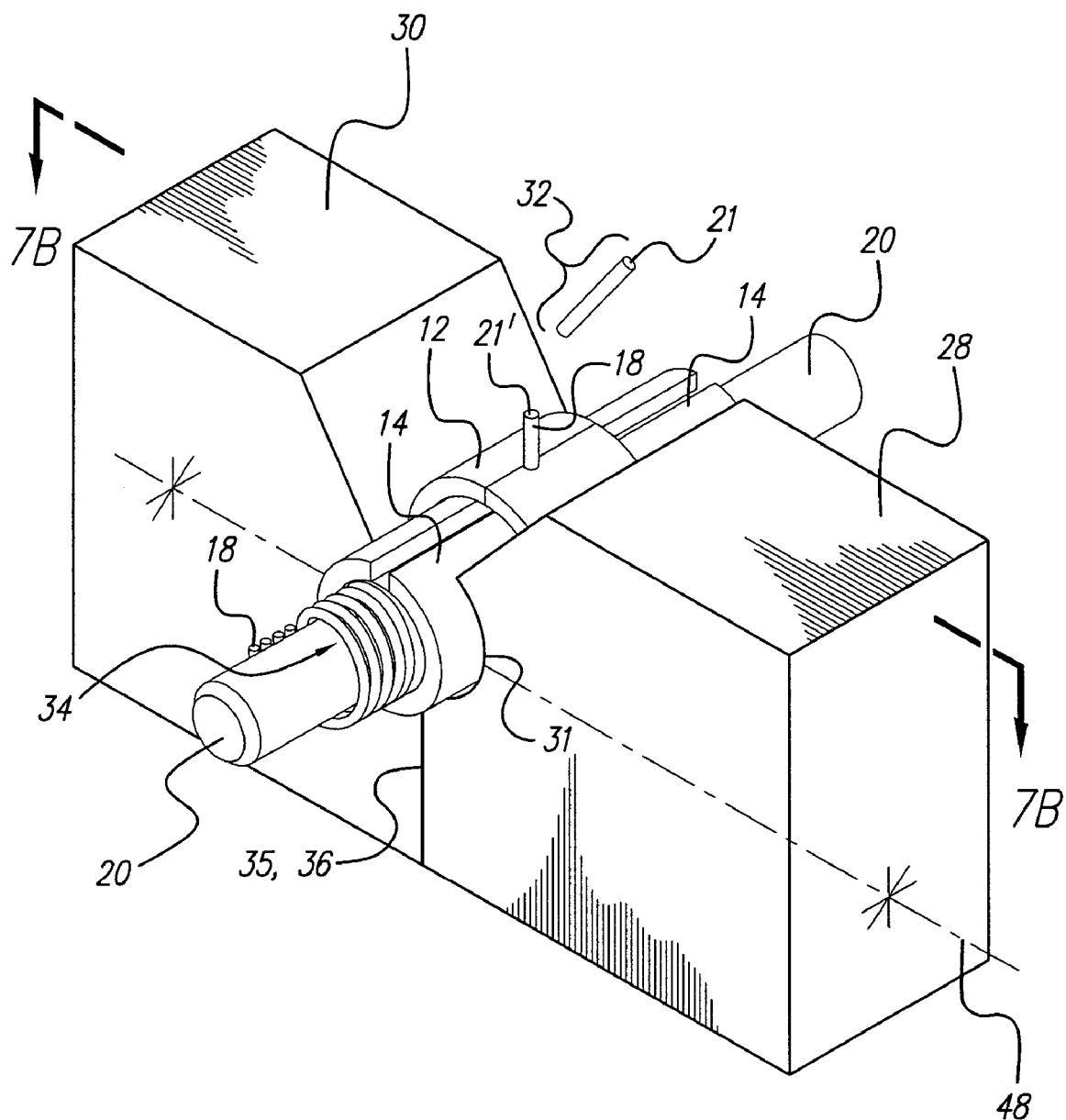
FIG. 7A shows a perspective view of the electrode array in the compressive die showing the lead wire being trimmed to a desired length.

As explained above, the electrode assembly shown in FIGS. 6A and 6B, consists of the lead wires 18, separation tube 14, and the ring contacts 12. The distal end (or pigtail) of each of the lead wires protrudes (in a general radial direction) from the gaps 24 and 22 of the separation tube 14 and ring contacts 12. At this point in the assembly process, the electrode array is positioned in the partial channel 31 formed between the left and right plates 28 and 30 of the compressive die, as shown in FIG. 6B, where the left and right plates function much like the jaws of a vice in holding the electrode array. FIG. 7A shows a section of the electrode array 10 positioned in the channel 31 formed by the left and right plates 28 and 30 of the compressive die. The left and right plates are compressed until the planes 35 and 36 contact each other. A tightening screw can be placed along the axis 48 in order to facilitate movement of the left and right plates. Since the material of the ring contact 12 is softer than the material of the multi-helix wire 18, as the opening gap x shown in FIG. 4A closes due to the crimping process from the compressive die, the ring contact 12 will conform around the multi-helix wire 18 forming a tight fit between the multi-helix wire 18 and the ring contact 12.

Figure 7B:
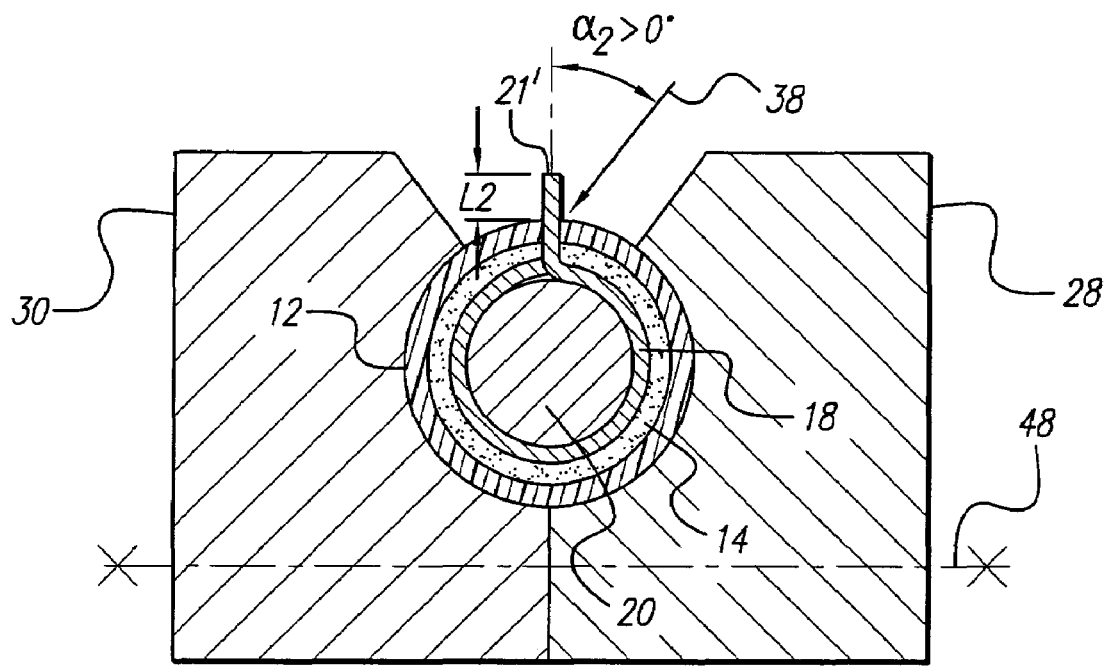
FIG. 7B is a cross sectional view taken along line 7B—7B of FIG. 7A, showing the compressive die and electrode array.

As further seen in FIG. 7A, once the electrode array 10 is held between the left and right plates, the pigtail portion 32 of the wire 18 is cut off, or removed, leaving a new stub end 21' of the lead wire 18. Typically, the stub end 21' protrudes radially out from the surface of the ring contact 12 a distance L2 (FIG. 7B). In the preferred embodiment, the distance L2 is about 0.1 mm. The pigtail portion 32 of the wire may also be completely trimmed off so that the distance L2=0.

Referring to FIG. 7B, there is shown a cross sectional view taken along the section line 7B—7B of FIG. 7A. FIG. 7B shows the new wire tip 21' having a distance of L2, which as indicated is typically about 0.1 mm, but may be flush with the surface of the ring contact 12 (L2=0). Each lead wire is typically trimmed to the same distance L2. The stub tip 21' is next laser welded to the ring electrode 12. The direction of the laser beam used to perform this weld is preferably as indicated by the arrow 38 in FIG. 7B. The angle α2 between the direction of the laser beam and the tip of the wire must be greater than zero as shown in FIG. 7B. Typically, this weld angle α2 will range from about 20 to 50 degrees.

The alignment of the left and right plates continues for all sections containing a ring contact. The trimming and welding process is individually done for all protruding wires. If the wires protrude in a non-alignment orientation as shown in FIG. 3B, using the aid of the mandrel 20, the pre-assembled electrode array is rotated for each assembled wire until the tip of the lead wires, 18A, 18B, 18C, or 18D are vertical relative to the compressive die as shown in FIG. 7B.

Figure 2:
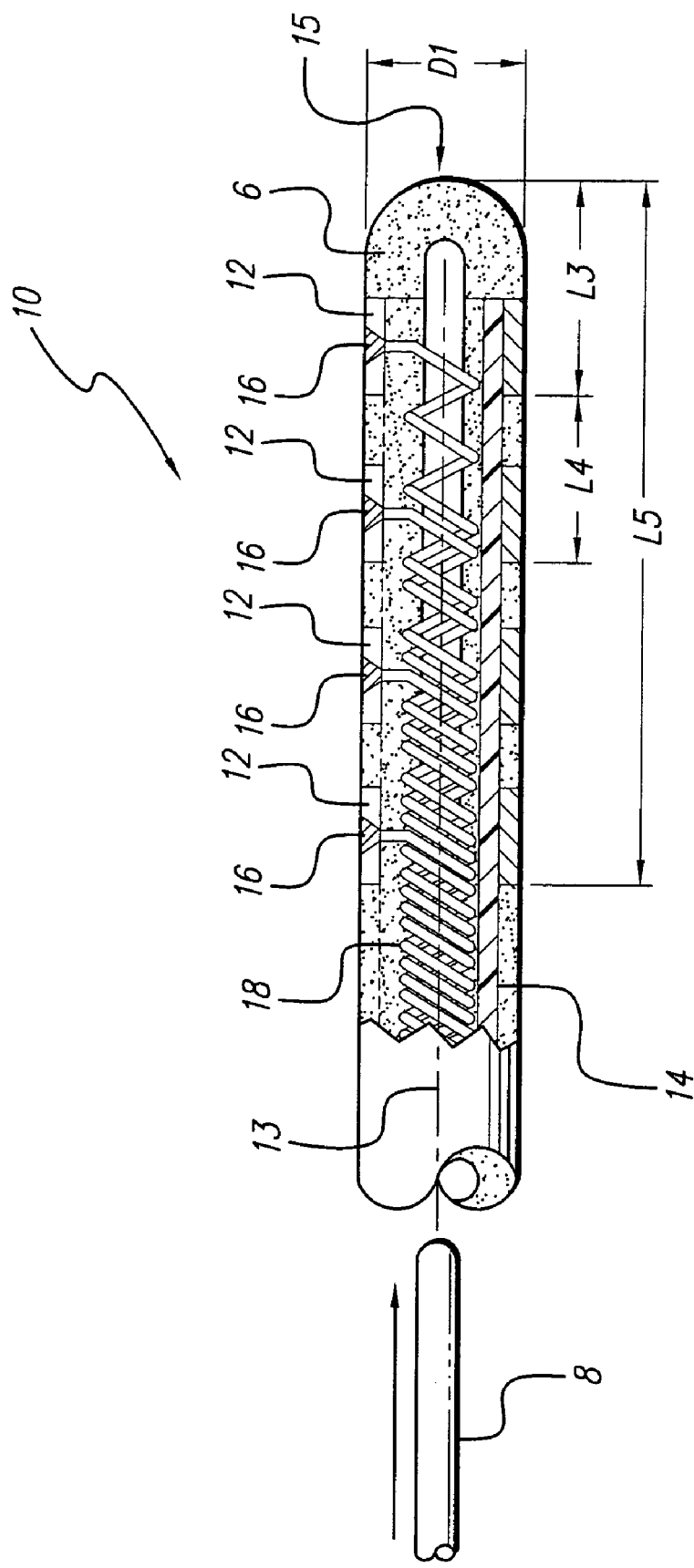
FIG. 2 is a longitudinal sectional view of the multicontact band type electrode array shown in FIG. 1.
Figure 7C:
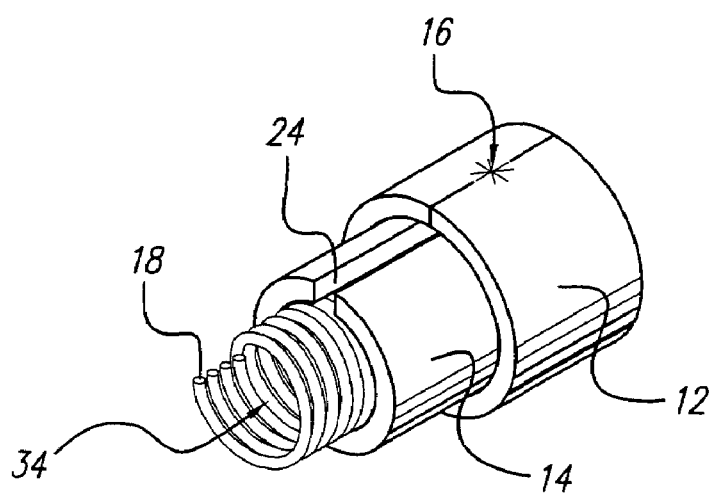
FIG. 7C shows a partial perspective view of the electrode array and further illustrates a typical location of the laser spot weld used to fuse the wire to the split band contact.

FIG. 7C shows a sectional perspective view of the electrode assembly including a typical laser beam weld 16. The ring contact 12 has been secured to the lead wire 18 by the laser beam weld 16. The welding process is performed to all of the trimmed lead wires 21' protruding from their corresponding ring contacts 12 or to those flush with the surface of the ring contacts 12. After the welding process, the ring contacts are securely positioned along the longitudinal axis 13 of the electrode array and are generally evenly spaced as shown in FIG. 2, where a cross section of the assembled electrode array is shown. After the entire welding process, the mandrel may be removed and replaced with a molding stylet 60. Also shown in FIG. 2, the first ring contact (i.e., the most distal ring contact) has a distance L3 from the distal end 15 of the electrode array. In the preferred embodiment, L3 is about 2.0 mm which also corresponds to the pitch P shown in FIG. 3. The second ring contact (i.e., second most distal ring contact) is located a distance L4 from the first ring contact, where L4 is typically about 2.0 mm. The contacts that follow would then have the same pattern, assuming equal spacing is desired. As an example, as shown in FIG. 2, four ring contacts 12 are spaced apart from the distal end 15 over a total distance of L5, where L5 is about 8.0 mm. It is to be understood that these dimensions, as well as other dimensions presented herein, are only exemplary of one embodiment, and are not meant to be limiting.

Still with reference to FIG. 2, it is seen that the overall diameter of the electrode array 10 is a distance D1. In the preferred embodiment, the diameter D1 is about 1.2 mm.

Figure 8A:
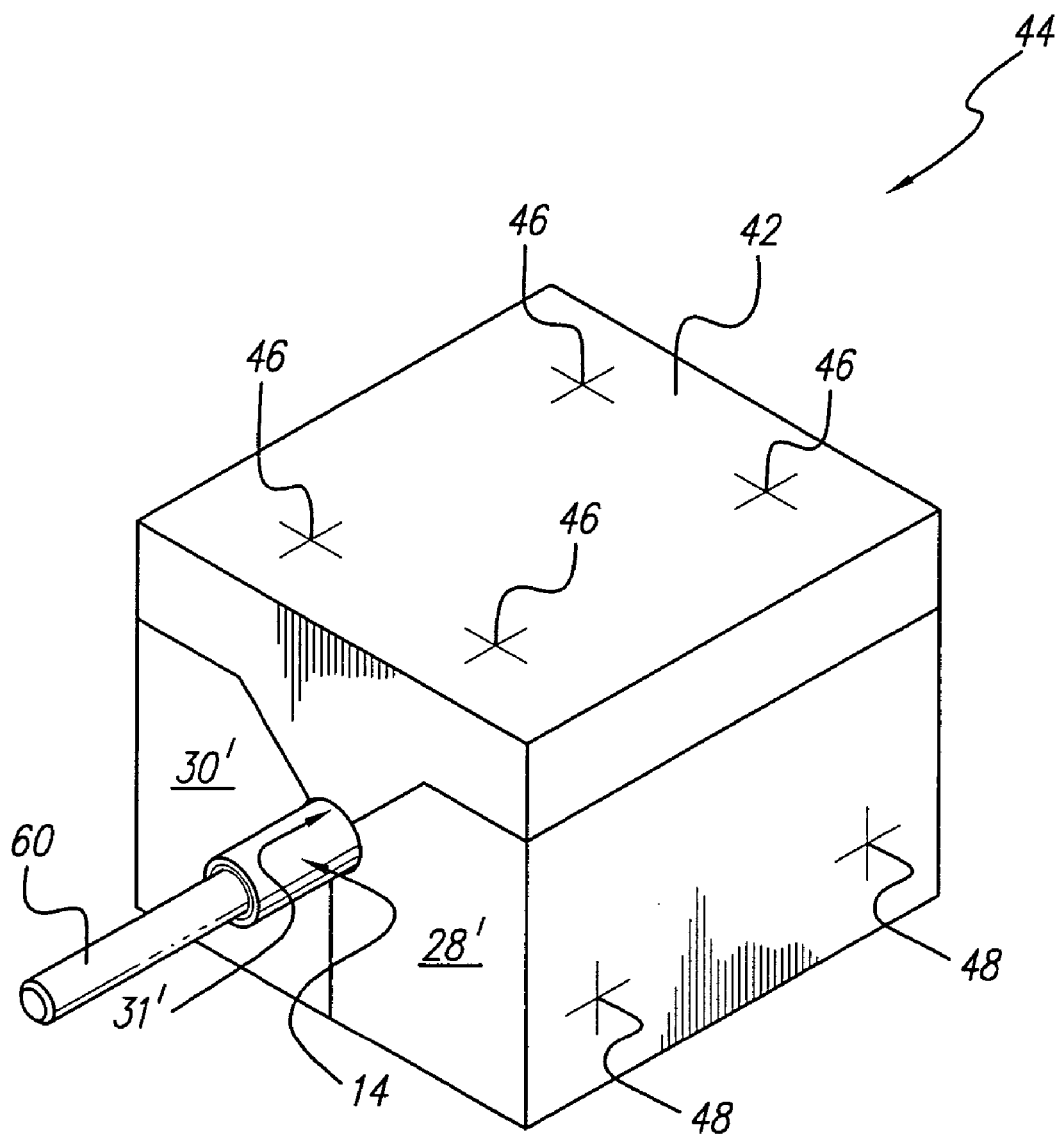
FIG. 8A shows a perspective view of the electrode array inside a molding die with a molding stylet protruding from the central lumen.

Next, with reference to FIG. 8A, a complete assembly is shown of a molding die 44 with the electrode array 10 and a molding stylet 60 protruding from the channel 31'. A top plate 42 of the molding die is firmly attached to the left plate 28' as well as to the right plate 30' using typical tightening screws which could be located in the vertical axis 46 of the top plate 42. The left plate 28' and right plate 30' may be similar to plates 28 and 30 used in the compression die shown in FIG. 6B. The difference would be that plates 28' and 30' would be longer in length so that the part of the electrode array which contains the electrode contacts can be positioned inside the entire central channel 31' formed by plates 28' and 30'. Positioning the electrode array inside the molding die 44 is necessary for completing the final manufacturing step of the multicontact electrode array 10.

Figure 8B:
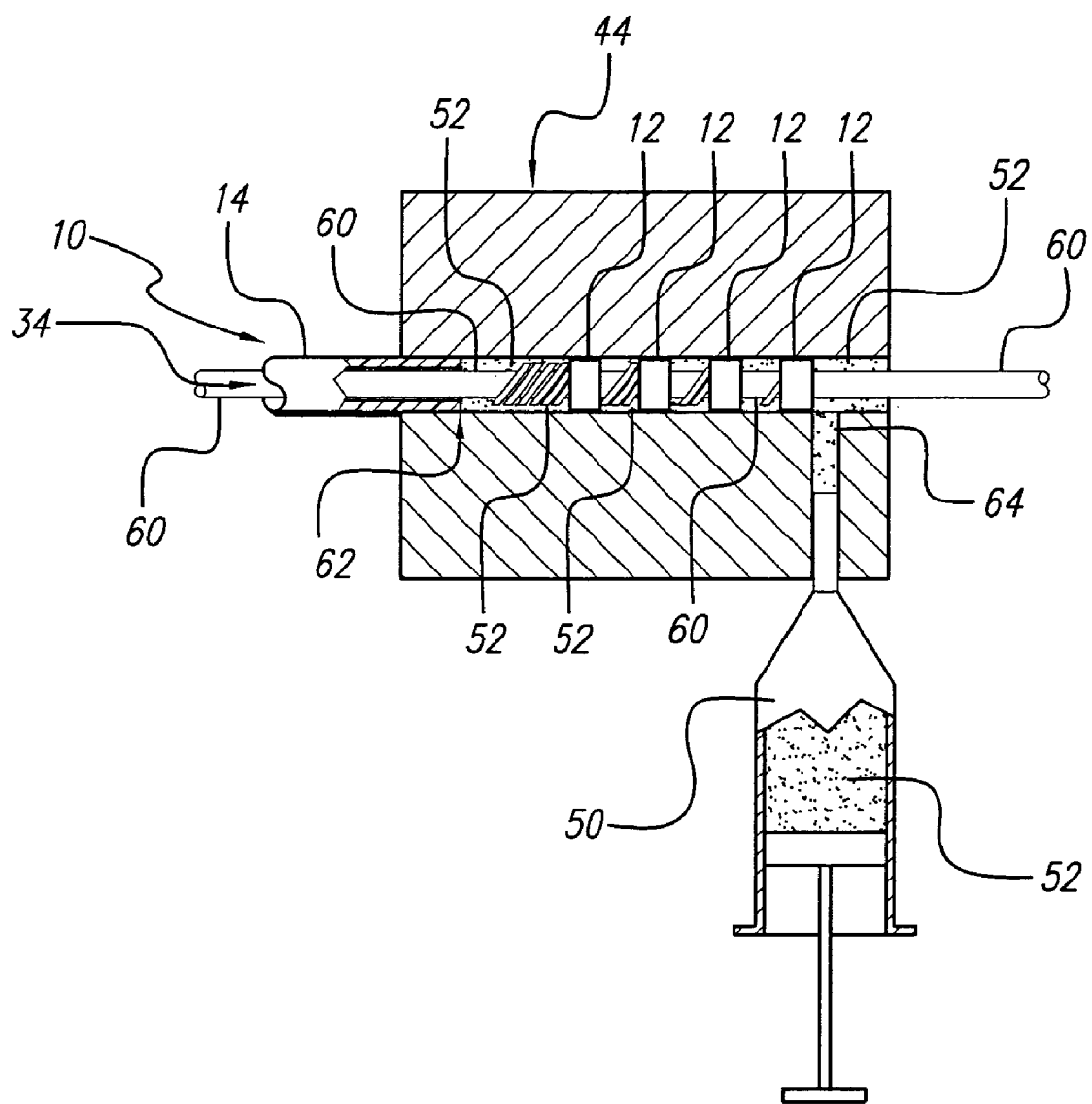
FIG. 8B shows a sectional view of the electrode array formed in the molding die of FIG. 8A with a molding stylet used to fill the central lumen, and further depicts the use of a backfilling polymer syringe to fill the internal gaps between the electrode array components.

FIG. 8B also shows the optional method in eliminating the separation tube 14 from the electrode array at the location of the contact rings 12. The distal end 62 of the separation tube is located close to the last contact ring 12. At this final step, a syringe tool 50 containing a supply of a polymer filler 52 is inserted into an access hole 64 in the bottom of the molding die, as shown in FIG. 8B. The polymer filler 52 is injected into the gaps formed by the pre-assembled electrode components. If desired, the die is shaped so as to form a rounded tip at the distal tip of the electrode array with the polymer filler 52. When the required amount of polymer filler material has been injected to fill the gaps, then the polymer is allowed to cure in a conventional manner. A suitable filler material, for example, is a type of silicone polymer or silicone rubber known as LSR-70. The properties of LSR-70 are well known in the art, and LSR-70 may be obtained commercially from numerous sources. LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C. for about 15 minutes.

The electrode array 10 and molding stylet 60 remain in the molding die 44 during the cure time which may vary depending on the length of the electrode array and how many ring contacts it may contain. Thus, it is seen that through proper use of the molding die 44, or other dies, the electrode array may be formed to assume a straight shape having a rounded cross section.

After the filler material (e.g., LSR 70) cures, the electrode array 10 and molding stylet 60 are removed from the channel 31' of the molding die 44 by loosening the screws holding the plates together. The molding stylet 60 is removed from the distal end of the assembled electrode array and the distal opening is sealed with a liquid polymer or pre-cured sealing plug 6 (shown in FIG. 2). The sealing plug 6 may be made from the same filler material. The electrode array 10 is then placed in a clean environment to remove and wash any excess residue. The electrode array structure is complete after it has been examined to quality standards.

During the manufacturing process of the electrode array 10, a central lumen 34 is thus formed through the entire length of the electrode array 10. This central lumen 34 serves the purpose of providing access for an insertion stylet 8 (shown in FIG. 2) to be used in conjunction with the lead during implantation of the electrode to the stimulating area.

As described above, it is thus seen that the present invention provides an electrode array that is easy to manufacture and which provides enhanced performance when used due to the alignment between the lead wire and ring contact. Such electrode provides an array of spaced-apart ring contacts along its longitudinal axis. The simple and reliable construction method of the described electrode array makes this invention a very cost-effective approach for manufacturing such a multicontact electrode array.

While the invention herein disclosed has been described by means of specific embodiments and applications thereof, numerous modifications and variations could be made thereto by those skilled in the art without departing from the scope of the invention set forth in the claims.

What is claimed is:

1. A method of making a multicontact electrode array comprising:
   a. forming on a mandrel a multiwire helically-wound configuration wherein each wire of the multiwire helically-wound configuration has a distal end that is bent to extend radially outward, and wherein the multiwire helically-wound configuration has an outer diameter;
   b. forming a separation tube having an inside diameter that is approximately the same as the outer diameter of the multiwire lead;
   c. positioning the separation tube over the helically wound multiwire lead and mandrel, the separation tube having a longitudinal slit at one end thereof through which the pigtail end of each wire extends;
   d. placing a plurality of open-ring contacts having an open axial gap snugly over the separation tube, with the pigtail end of each wire extending through the axial gap of a respective open-ring contact;
   e. using a compressive die to firmly close the gap between the ring contacts and the pigtail end of each wire;
   f. electrically and mechanically bonding the pigtail end of each wire to the open-ring contact;
   g. removing the mandrel from the central lumen and replacing it with a molding stylet;
   h. placing the pre-assembled electrode array and molding stylet in a molding die;
   i. filling all internal gaps formed by the electrode components with a polymer filler material through an access hole in the molding die;
   j. curing the polymer filler material;
   k. removing the molding stylet to form a central lumen in the electrode array.

2. The method of claim 1 wherein electrically and mechanically bonding the pigtail end of each wire to an open-ring contact comprises
   trimming the pigtail to a desired length, and
   laser welding the wire to the ring contact.

3. The method of claim 2 further including positioning the assembled multiwire lead, separation tube, and open ring contacts in a compressive die prior to trimming the pigtail lead to a desired length, and applying a sufficient compressive force to the open-ring contact so as to close the open-ring contact firmly against the pigtail lead passing through the axial gap.

4. The method of claim 3 wherein the ring contact is made from a compressible material, and wherein the method further includes closing the open ring contacts with sufficient compressive force so as to compress the ring contact into the body of the separation tube and closing the gap between the ring contact and the lead wires.

5. The method of claim 2 further including closing the distal end of the electrode array to form a rounded tip.

6. The method of claim 5 wherein closing the distal end of the electrode array comprises applying a liquid polymer to the distal end of the electrode array, and allowing the liquid polymer to cure.

7. The method of claim 5 wherein closing the distal end of the electrode array comprises applying a pre-cured plug made from the same material as the filler molding material to the distal end of the electrode array.

8. The method of claim 1 wherein forming the multiwire helically wound configuration comprises placing the multiwire helically wound configuration on a mandrel, and unwrapping the distal end of each wire to form a distal protruding tip.

9. The method of claim 8 further including unwrapping the distal end of each wire to achieve a desired axial separation or pitch between the distal protruding tips.

10. The method of claim 9 further including trimming the distal protruding tips of each wire to a desired length.

* * * * *